United States Patent [19]

Chakeres

[11] Patent Number: 5,690,108
[45] Date of Patent: Nov. 25, 1997

[54] INTERVENTIONAL MEDICINE APPARATUS

[76] Inventor: Donald W. Chakeres, 2274 Club Rd., Columbus, Ohio 43221

[21] Appl. No.: 804,062

[22] Filed: Feb. 21, 1997

Related U.S. Application Data

[63] Continuation of Ser. No. 345,243, Nov. 28, 1994, abandoned.

[51] Int. Cl.⁶ .................................................. A61B 5/05
[52] U.S. Cl. .................. 128/653.1; 606/130; 378/20; 378/205
[58] Field of Search .................. 128/653.1, 653.2, 128/653.5, 662.05; 606/130; 604/116; 378/20, 68, 162, 163, 177, 195, 204, 205

[56] References Cited

U.S. PATENT DOCUMENTS

| | | | |
|---|---|---|---|
| 4,638,798 | 1/1987 | Sheldon et al. | 128/653.1 |
| 4,722,336 | 2/1988 | Kim et al. | 378/162 |
| 4,750,487 | 6/1988 | Zanetti | 606/130 |
| 5,053,042 | 10/1991 | Bidwell | 606/130 |
| 5,142,559 | 8/1992 | Wielopolski et al. | 378/205 |
| 5,147,372 | 9/1992 | Nymark et al. | 128/653.1 |
| 5,309,913 | 5/1994 | Kormos et al. | 128/653.1 |
| 5,383,454 | 1/1995 | Bucholz | 128/653.1 |

Primary Examiner—Marvin M. Lateef
Assistant Examiner—Brian L. Casler
Attorney, Agent, or Firm—Thomas S. Baker, Jr.

[57] ABSTRACT

Apparatus for assisting in the manual location, vectoring, and insertion of a medical instrument relative to a patient's body using medical imaging equipment providing a cross-sectional imaging plane and a monitor which displays a distance calibrated cross-section imaged at the equipment imaging plane of the patient and an apparatus reference pattern. The displayed image sets forth the actual distance and angular orientation between the image plane and a reference axis of the device pattern to physically define a point on the pattern that corresponds to a point on the image.

12 Claims, 15 Drawing Sheets

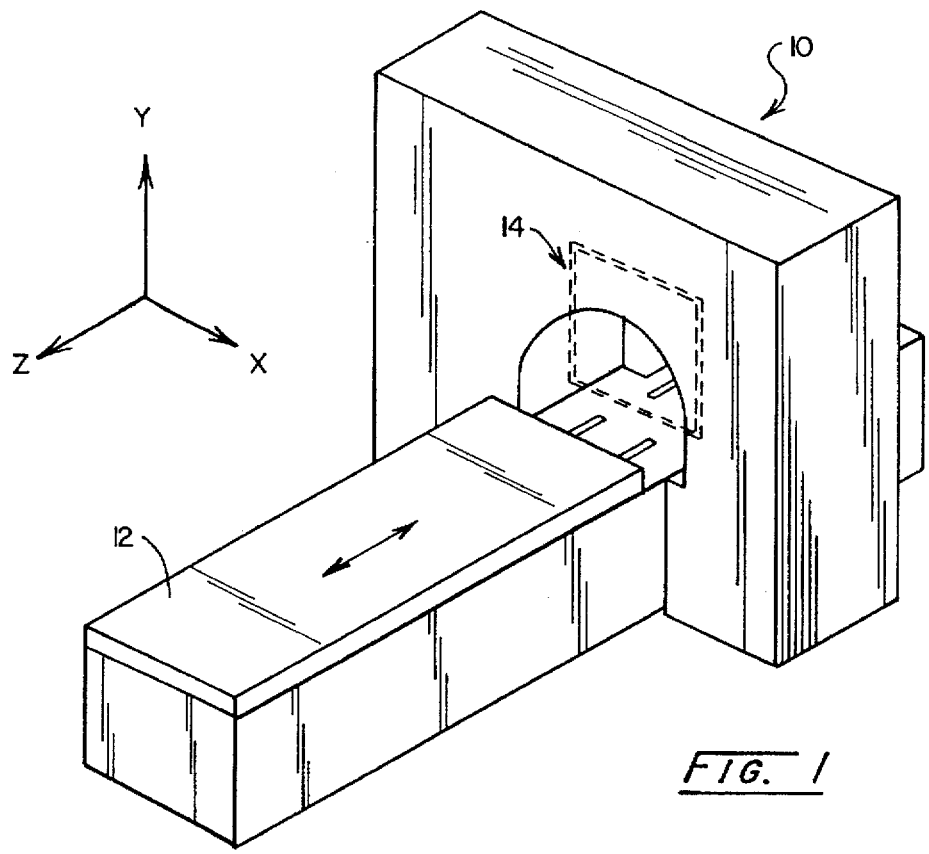
FIG. 1
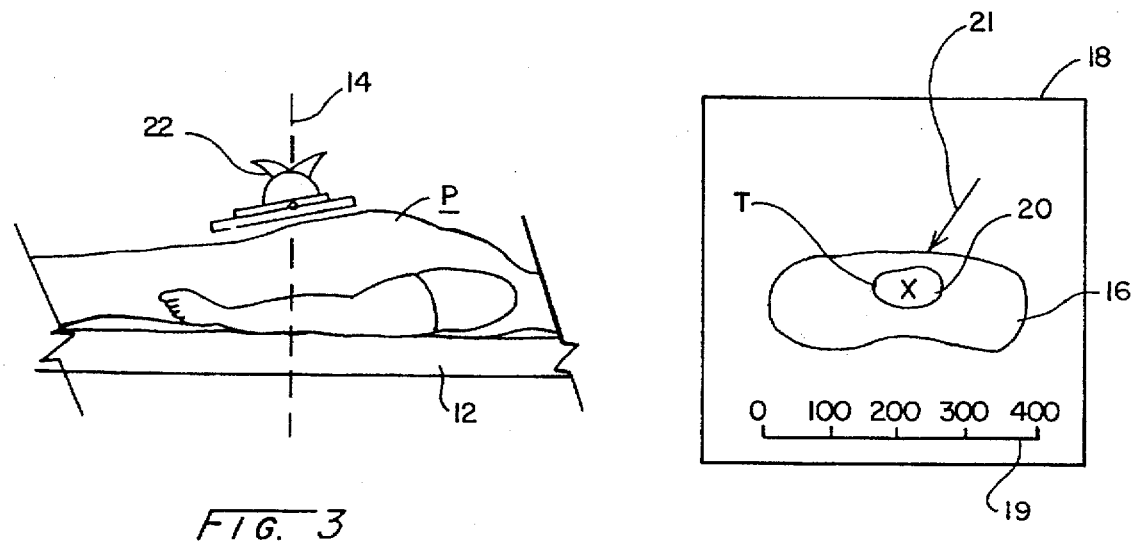
FIG. 3
FIG. 2

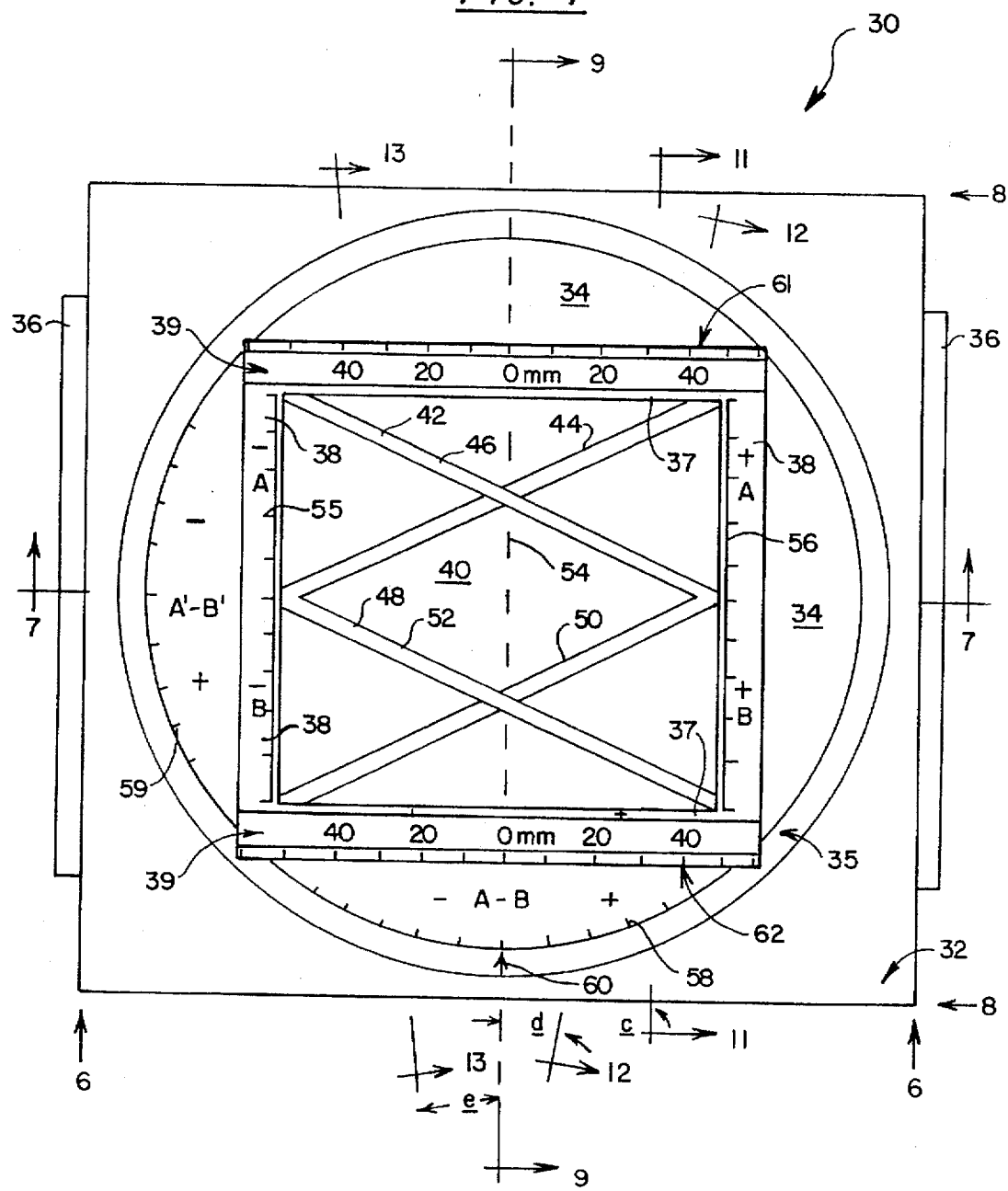

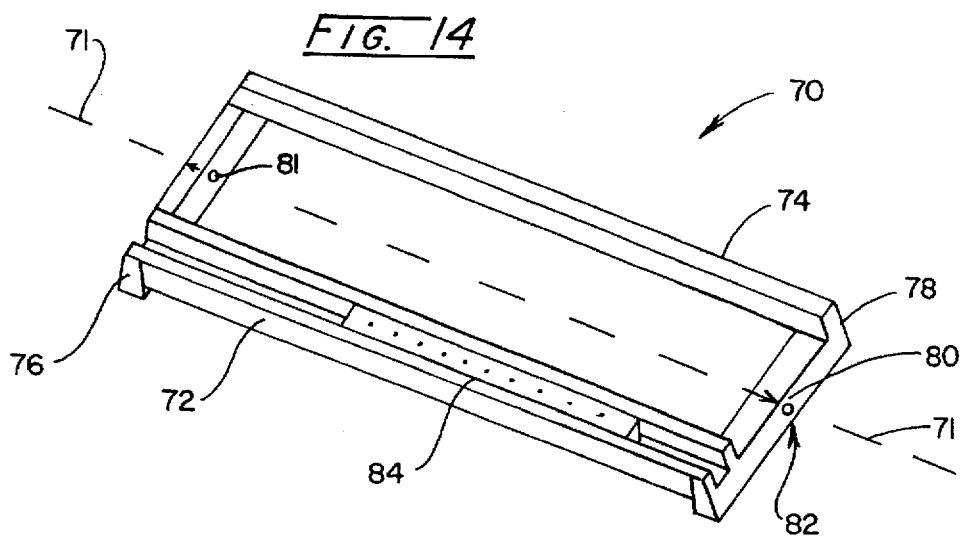
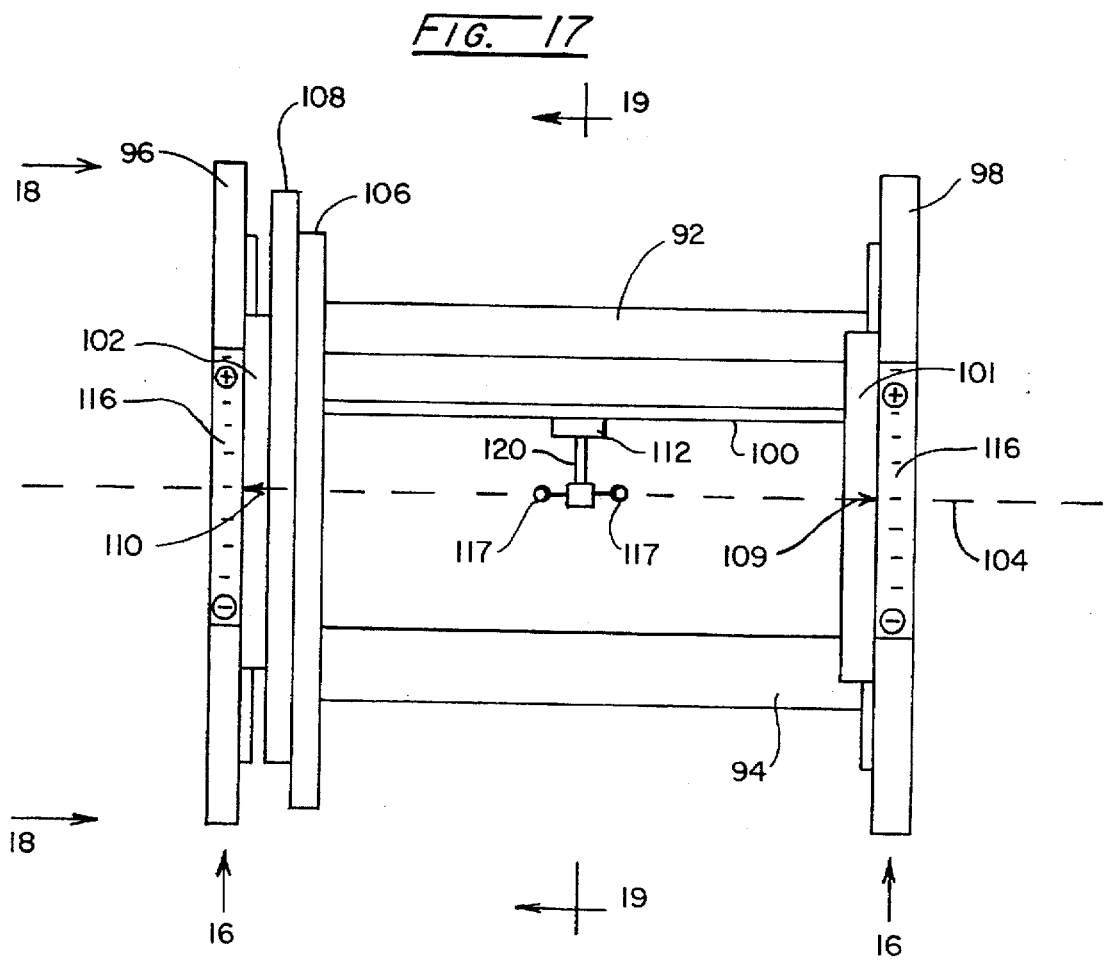

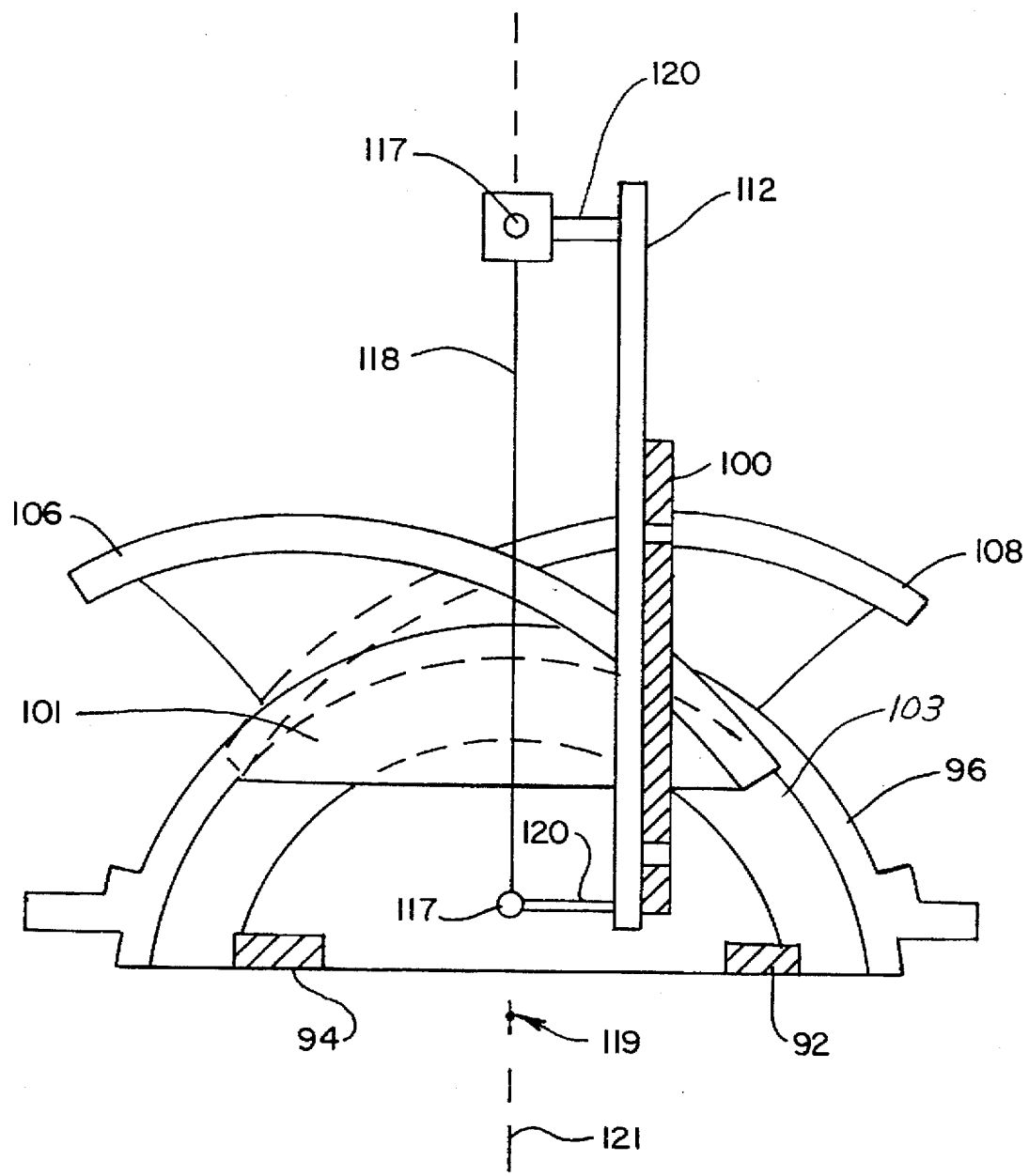

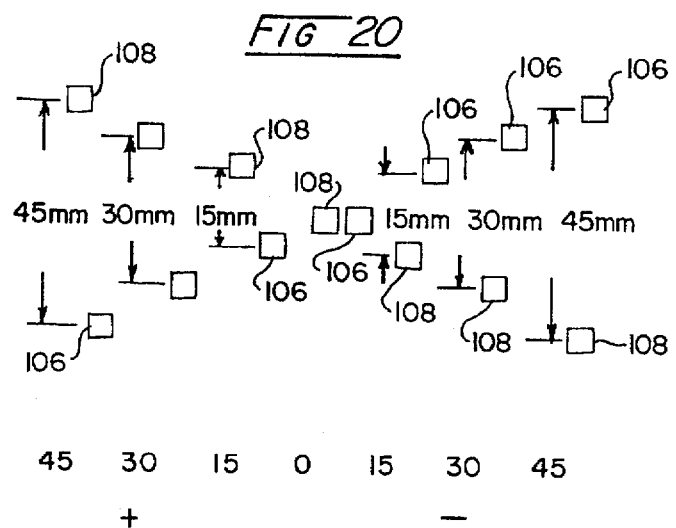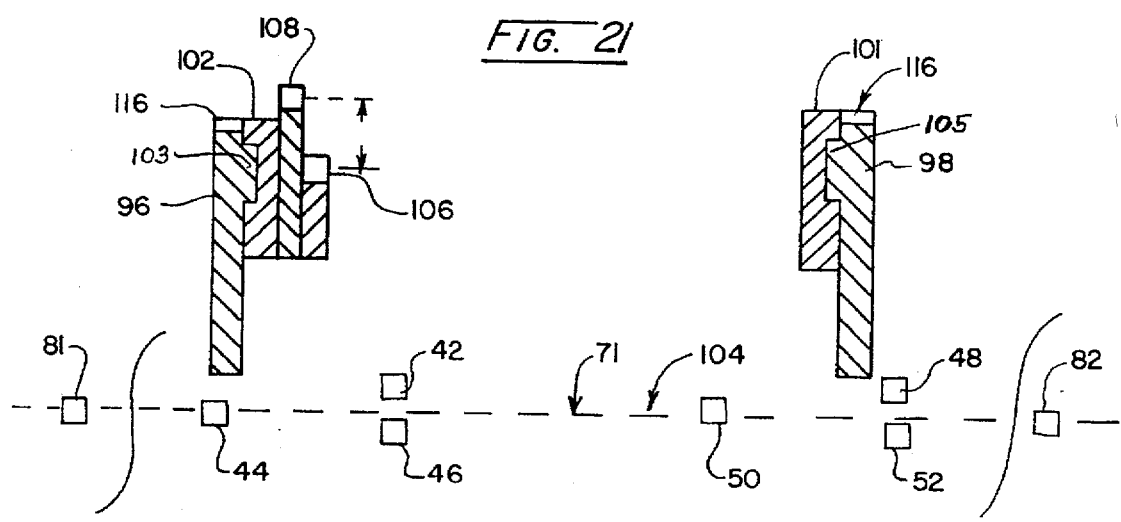

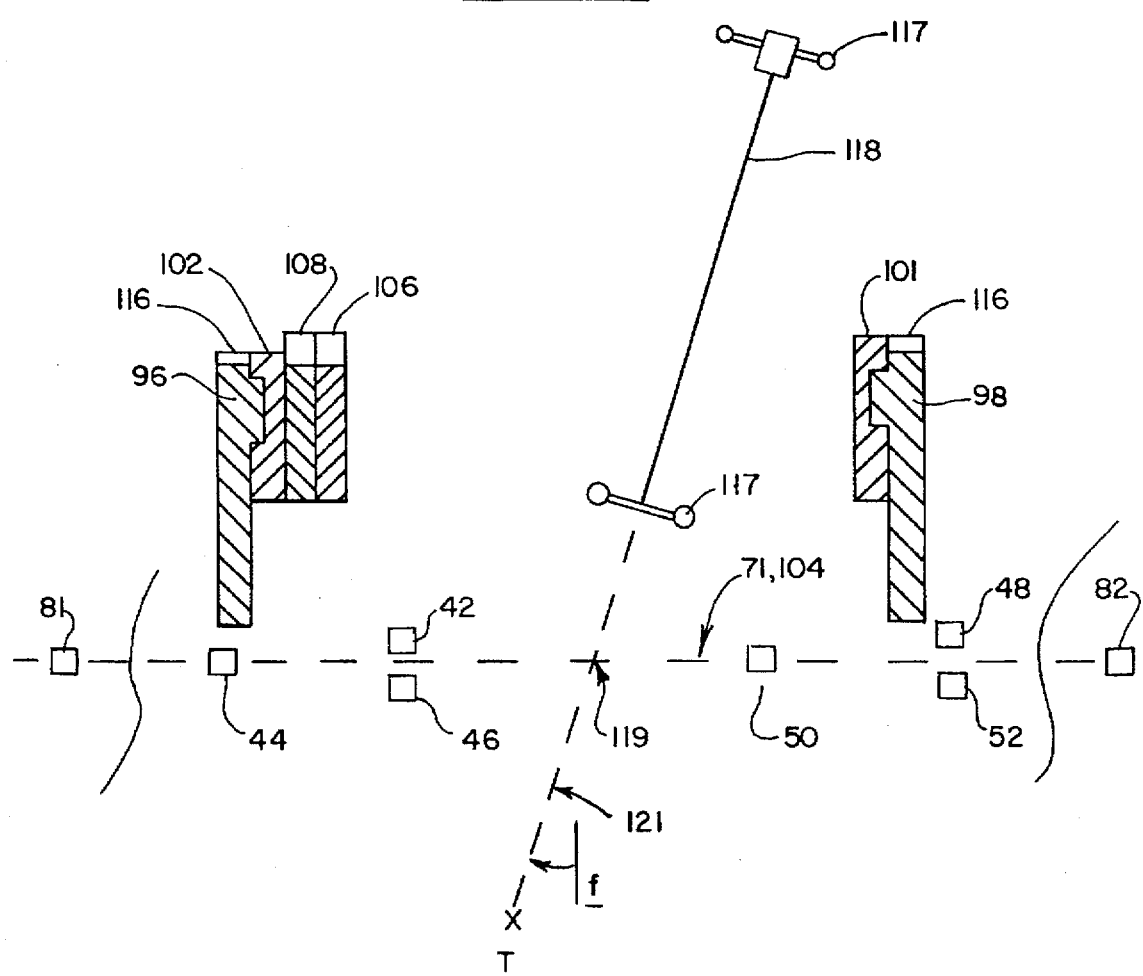

INTERVENTIONAL MEDICINE APPARATUS

CROSS-REFERENCES

This application is a continuation of application Ser. No. 08/345,243 filed Nov. 28, 1994 now abandoned.

FIELD OF THE INVENTION

This invention relates generally to interventional medicine, and particularly concerns apparatus which may be advantageously utilized by a physician in cooperation with cross-sectioning types of medical imaging equipment, such as computed tomography (CT) imaging equipment or magnetic resonance (MR) imaging equipment. The invention may be utilized to conveniently and accurately aid in timely (realtime), manually, truly, and physically accomplishing the steps of locating, vectoring, and inserting a needle-like medical device at, toward, and in a patient's targeted anatomic feature.

BACKGROUND OF THE INVENTION

Medical science researchers and practitioners are increasingly giving more attention to the development of less-intrusive diagnostic and therapeutic medical procedures for use in the care of patients, thereby avoiding otherwise required conventional surgery and the consequent high costs of patient hospitalization. Examples of such less-intrusive diagnostic and therapeutic procedures include laparoscopic surgery, placement of drainage catheters, fine needle aspiration biopsies, stereotactic radiation therapy, needle injection of drugs (including radiological drugs), soft tissue destruction, trocar insertion of cannulae, and the like, each accomplished in relation to a particular patient's anatomic target and preferred vector path.

Medical equipment manufacturers have also given attention to the development and marketing of apparatus for use in effecting less-intrusive diagnostic and therapeutic medical procedures, and often such apparatus is comparatively complex in design, costly to obtain, and difficult and time-consuming to utilize. U.S. Pat. No. 4,341,220 issued in the name of Perry, for instance, discloses a rigid, four-sided rectangular framework which when utilized in cooperation with CT scanning equipment functions to develop, by computer calculation, stereotactic coordinate information which is used as an input for secondary-device execution of a desired interventional procedure at a distant later time and at another location. The apparatus is not suitable for use interactively in the execution of a diagnostic or therapeutic medical procedure.

U.S. Pat. No. 4,346,717 issued in the name of Haerten teaches interventional medical apparatus using ultra-sound sensing technology and having a complex electronic circuitry arrangement for calculating a guide beam display. The apparatus does not directly image the interventional procedure probe.

U.S. Pat. No. 4,618,978 granted to Cosman discloses a three-dimensional cubic framework which when imaged by sectional plane cuts provides intercept indications that, when all such cuts are reassembled in a computer simulation, are used to calculate the coordinates of the selected anatomical target. The device does not accomplish a true physical alignment with the equipment scanner.

U.S. Pat. No. 4,722,336 issued in the name of Kim et al. teaches apparatus for use in a fluoroscopy imaging system and involves interactive interventional probe manipulation relative to two cross-intersecting projection X-ray images. True cross-sectional images are not utilized in any manner—only intersecting projected images.

U.S. Pat. No. 4,930,525 to Palestrant teaches an interventional medicine needle insertion method suitable for use with CT imaging equipment only and requires a computation, by CT scanner computer, of distances and angles and a subsequent relating of those distances and angles to light beam reference lines in order to utilize a hand-held and leveling-required guide element having adjustable angle features. Light beam reference lines are not always available, especially in the case of MR imaging equipment. The Palestrant method displays an image of the inserted needle-like medical instrument on the imaging equipment monitor (display screen) since the instrument is positioned in the equipment imaging plane.

U.S. Pat. No. 5,050,608 issued in the name of Watanabe et al. discloses a computer-controlled articulated arm which is useful for designating on a CT image articulated arm tip points which are a result of calculation and not reality.

U.S. Pat. No. 5,098,383 issued in the name of Hemmy et al. teaches a three-step interventional procedure which first involves obtaining patient-specific tissue geometry and practitioner requirement information, subsequently involves the design and manufacture of a non-adjustable guide for the specific application, and lastly involves the use of that non-adjustable guide to accomplish the sought interventions such as drilling holes to receive spinal screws that secure a plate to thereby fuse adjacent vertebrae. The system monitor displays previously-acquired location and vectoring information and does not develop that information in the system scanner.

U.S. Pat. No. 5,221,283 issued in the name of Chang and assigned to General Electric Company discloses apparatus and methods for stereotactic surgery in which stereotactic information obtained at an earlier time and for a different site is utilized in complex computer calculations to specify a surgical tool trajectory. The device has at least two major shortcomings since it cannot be used with CT or MR imaging equipment during equipment imaging operation, and there is no real-time or near real-time imaging confirmation of procedure progress accuracy.

To overcome the limitations of the known apparatus and related medical procedures I have discovered a novel apparatus arrangement and applicable utilization method steps which obtain important advantages over the prior art. The subsequently disclosed and claimed invention is relatively simple and inexpensive to manufacture and use, does not require either time-consuming calculations, or computer or other machine computation, or a secondary execution device or devices to derive location coordinate information for placement and vectoring purposes, and, depending upon imaging equipment (CT or MR for example) operating characteristics, conveniently permits either real-time or near real-time monitoring of medical instrument placement, vectoring, and insertion progress potentially within the imaging system. It is designed to need only a few images to physically orient the chosen vector path.

Other advantages and objects of the invention will become apparent during a careful and thoughtful consideration of the descriptive materials which follow.

SUMMARY OF THE INVENTION

The present invention basically involves, in addition to the use of a cooperating, cross-sectional type (CT or MR) medical imaging system, use of an assist apparatus essentially comprised of a base subassembly, an image-conspicuous reference pattern either integrated with or separately supported on the base subassembly, and a calibrated instrument vectoring guide that is linearly and angularly movable with respect to the apparatus base subassembly. The apparatus base subassembly is appropriately located near, or upon, that region of the patient's body that is to be sectionally imaged, and need only be initially approximately correctly oriented relative to the sectioning plane and region of interest within the patient.

The apparatus base subassembly in one embodiment of the invention includes a frame element having a principal linear axis and a specifically-designed, image-conspicuous planar reference pattern with an accompanying calibrated adjustment motion path. Such reference pattern is cross-sectioned and imaged by the medical imaging equipment during patient cross-sectional imaging. The frame element is carried by a support and is rotatable relative to both the support and the patient's body about a substantially vertical axis that need not be initially or precisely perpendicular to the imaging equipment horizontal plane. In a disclosed second embodiment of the invention, the reference pattern element is combined with the instrument vectoring guide and is essentially only indirectly supported by the base subassembly. Each degree of motion of the moving elements of the invention has a calibrated motion path and a corresponding visible pattern plane on each image.

The frame element planar reference pattern has a characteristic configuration that encodes the separation distance or angularity of the reference pattern principal axis of symmetry relative to the imaging equipment sectioning plane X-Y or cross-sectioning plane if nonalignment exists, such distance or/and angle information being obtained by inferential interpretation of the displayed reference pattern images solely using direct image measurements, simple logic, and simple arithmetic for an interactive procedure. Calibrated scales provided integral with the frame element to measure angularity and cross-sectional plane displacements relative to the pattern principal axis of symmetry and are then utilized to manually or by remote control accurately physically locate adjacent to the patient's body the position of the imaging equipment sectioning (X-Y) plane. The separation distances and/or angles derived from the displayed reference pattern images correspond to the distances and angles on the frame element calibrated scales.

Next an apparatus track element, which in the second embodiment of the invention is combined with the first reference pattern element, is placed on the base frame element and is positioned so that its longitudinal axis of symmetry is contained in the imaging equipment sectioning (X-Y) plane. The apparatus vectoring aid is then moved relative to the track element, if desirable, and is subsequently utilized by the attending physician to manually and accurately define a preferred vector path or advance the medical needle-like instrument toward the selected anatomic target.

As more fully described in the drawings and detailed description which follow, the apparatus vectoring aid subassembly includes an adjustable vectoring plane element which is supported by the rotatable subassembly base element, two different image visible reference patterns, and needle localizers which, during patient cross-sectional imaging, are imaged and shown on the imaging equipment cross-sectional display.

One of the vectoring plane element image visible references appears on the imaging equipment display to indicate the selected position of one vector-defining point through which the physician operator will manually advance the needle-like medical instrument for contact with the patient's body and penetration toward the patient's selected anatomical target which is a second vector-defining point.

The other of the vectoring plane element image visible references is in the form of the "Warped-X" reference pattern described more specifically in the detailed description which follows. Such other vectoring plane element image visible reference pattern provides a scaled indication of angular misalignment of the vectoring plane element relative to the imaging equipment cross-sectional (X-Y) imaging plane, if present, on the imaging equipment cross-sectional image display. The using physician may conveniently make any correction necessary so that the two planes are in the ideal positional agreement.

Additionally, the vectoring plane element is provided with an appropriately positioned protractor-like angular scale or its equivalent which the physician uses to properly orient the to-be-inserted needle-like medical device in the equipment cross-sectional (X-Y) plane to achieve the desired path to the selected anatomic target. A determination of the appropriate angle of entry through the displayed vectoring plane element axis of rotation gap and angle of insertion and progress of the procedure is determined from a visual inspection of the imaging equipment cross-sectional image display and the use of an angle-measuring transparent overlay conveniently superimposed on the display. The calibrated motion and vector direction of the needle is also displayed on the image by needle localizer structures and a calibrated needle track path.

Lastly, it is important that through use of the invention apparatus the physician be able to readily monitor, in real-time, or in near real-time depending upon the type of imaging equipment being used, the accuracy of device placement, vectoring, and projection merely by a careful inspection and interpretation of the imaging equipment cross-sectional (X-Y plane) image reference pattern display.

Other advantages associated with my invention will become apparent from the drawings and detailed description which follow.

DESCRIPTION OF THE DRAWINGS

FIG. 1 is a schematic perspective view of CT medical imaging equipment showing the relationship between a patient support and the equipment cross-sectional imaging plane and their relationship to applicable mutually perpendicular coordinate planes;

FIG. 2 is a schematic view of a typical patient cross-sectional image as displayed by the monitor of the equipment arrangement of FIG. 1;

FIG. 3 is a partial elevation view illustrating the positioning of a preferred or first embodiment of the assist apparatus of this invention in proximity to a region of interest of a patient's body for immediate use in a physician-controlled diagnostic or therapeutic procedure utilizing the type of medical imaging equipment illustrated in FIG. 1;

FIG. 4 is a plan view of a base subassembly incorporated into the assist apparatus of FIG. 3;

FIG. 14 is a perspective view of the track subassembly incorporated into the assist apparatus of FIG. 3;

FIG. 17 is a plan view of the vectoring aid subassembly (FIG. 16) incorporated into the assist apparatus of FIG. 3;

FIG. 19 is a partial section side view of the vectoring aid subassembly along line 19—19 FIG. 17;

FIG. 20 is an illustration of the range of measured reference images which may be displayed on the imaging equipment monitor as a consequence of the FIGS. 16–19 planar reference pattern element being intersected by the imaging equipment imaging plane at different vector plane element relative angles through the axis of rotation;

FIG. 21 is a schematic sectional view of an imaging equipment monitor screen display illustrating the image displayed when the plane of the vectoring aid subassembly vector plane element is not contained within the imaging equipment imaging plane, line 21—21, FIG. 18;

FIG. 22 is a section view illustrating the image displayed on the imaging equipment monitor when the plane of the vectoring aid subassembly vector plane line 22—22 FIG. 18 is contained within the imaging equipment imaging plane;

DETAILED DESCRIPTION

Figure 5:
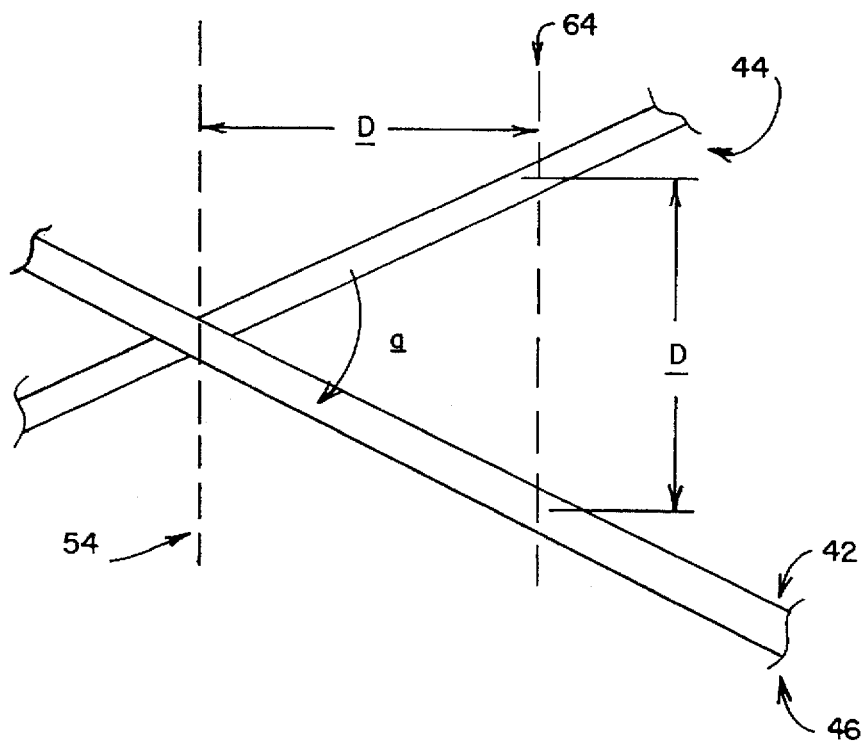
FIG. 5 is an enlarged plan view of a portion of FIG. 4 illustrating key pattern dimensional relationships.

FIG. 1 of the drawings schematically illustrates a unit of computed tomograph type (CT) cross-sectioning medical imaging equipment (10) with which the present invention may be cooperatively utilized. As previously suggested, equipment (10) might also take the form of a unit of magnetic resonance (MR) type of medical imaging equipment or other body cross-sectional system. Such equipment typically is provided with a scanning table (12) upon which the patient to receive treatment is appropriately positioned. In some equipment arrangements, the table (12) is incrementally indexed along its longitudinal axis to any of numerous different and repeatable positions at which the cross-sectional imaging plane (14) of the equipment intersects the patient's body at different points of interest. In other forms of such medical imaging equipment, the scanning table (12) remains in a transiently fixed position and the equipment scanner and cross-sectional imaging plane (14) are moved relative to the table (12) as a gantry. In the case of MR imaging equipment, images of many different patient sectional planes can be obtained without moving either the patient or the equipment so long as the patient's body region of interest is located generally in the center of the equipment magnet/magnetic field. Also, FIG. 1 additionally schematically illustrates the conventional X-Y-Z coordinate axis scheme that pertains to equipment (10) and that is sometimes referred to describe particular angular and directional relationships. Note that the equipment cross-sectional imaging plane (14) corresponds to the X-Y coordinate plane and that the longitudinal axis of the scanning table (12) is parallel to or along the Z coordinate axis.

FIG. 2 schematically illustrates a representative midsection body cross-sectional image (16) typically produced by equipment (10) for display on equipment monitor (18) to disclose internal tissue details. Depending upon physician interpretation of the displayed patient body image, the internal image area (20) may be selected as the body locale for subsequent interventional diagnostic or therapeutic medical treatment. Throughout the subsequent description it is predicated that imaging equipment (10) is operating in a mode whereby the images displayed on monitor (18) have a scale of true linear dimension (19) compared to the imaged structures and anatomical features. A centimeter reference scale such as image (19) is normally continuously displayed on the screen of monitor (18) for use in making image measurements. Also, in FIG. 2 and in some of the additional Figures, a selected or preferred target point T for use in locating the vector along which the medical instrument is to be manually guided during subsequent patient treatment is represented by a cross-hairs symbol. Additionally, the directional line of a preferred vector chosen by the operator is illustrated in FIG. 2 and designated 21.

To assist an attending physician in carrying out the subsequent interventional medical treatment, which typically involves the accurate placement, vectoring, and body insertion of a needle-like medical instrument such as a drainage catheter, for example, I have discovered that the hereinafter detailed assist apparatus (22) may be advantageously utilized. Apparatus (22) requires initial placement only near or in proximity to the patient body region of interest; it does not need, but may have, initial placement on, above, or around the target zone. As shown in FIG. 3, apparatus (22) is mounted directly on the patient or supported in a relatively fixed position by an accessory support assembly (23) (see FIG. 28 for details) mounted on or carried by table or gantry (12) and its placement is above the upper surface of the patient's body P and centrally over the imaged body internal structure (20) selected for diagnosis or therapy. Equipment table (12), apparatus (22), and patient P may then be moved as an entity to a position whereat equipment cross-sectional imaging plane (14) intersects assist apparatus (22) and displays a cross-sectional image on the equipment monitor (18) of both the patient's internal area (20) and superimposed apparatus (22). It is important to emphasize that assist apparatus (22) need not be positioned, and generally is not positioned, to have its principal base and reference pattern planes oriented precisely (e.g., parallel or perpendicular) with respect to the equipment coordinate planes. Also, apparatus (22) may alternatively be temporarily fixed in position on the patient's body P by the appropriate use of readily removable adhesive tape or removable insertion pins. Such "temporary fixation" minimizes the likelihood of apparatus (22) accidentally being moved relative to the patient's body P during use.

Apparatus (22), as will be noted from the descriptive material which follows, is basically comprised of a base subassembly (30) (FIGS. 4 through 13) positioned adjacent the patient's body P, a track subassembly (70) (FIGS. 14, 15) carried by the base subassembly, and a vectoring aid subassembly (90) (FIGS. 16 through 22) mounted upon the track subassembly. Manual placement, vectoring, and insertion of the needle-like medical instrument selected by the attending physician primarily involves cooperation of the medical instrument with features of vectoring aid subassembly (90).

Referring to FIG. 4, base subassembly (30) is basically comprised of a generally square support element (32), a cooperating circular frame element (34) carried by and rotatable relative to the support element, and an annular and movable position reference ring (35) carried by and rotatable relative to support element (32) and also frame element (34). Support element (32) is provided at the opposite side with outwardly projecting integral tongue elements (36) that cooperate with groove elements provided in accessory support assembly (23).

Most importantly, frame element (34) has integral rectangular upper scaled tracks and supports (37, 38, 61, 62), and within that upper portion is a lattice-like planar reference pattern (40) having a "double-X" configuration. Rod members (42, 44, 46) constitute one "X" (A) of the "double-X" reference pattern, and rod members (48, 50, 52) constitute the other "X" (B) of the pattern. Such reference pattern has a principal axis of symmetry (54) which, when apparatus (22) is initially placed upon patient P, is usually at best only somewhat parallel to the X-Y cross-sectioning plane (14) of imaging equipment (10). Also, frame upper portion (38) is provided with two fixed peripheral linear scales (55, 56) that each have graduations calibrated to indicate millimeter (mm) distances. Two other orthogonal movable peripheral scales (61, 62) on movable tracks help define the relation of the image section plane (14) and the lattice-like planar reference pattern (40). The peripheral scale (56) is fixed and an integral component of support (38). The peripheral scales (61, 62) and the side support of the lattice-like planar patterns (37) form a calibrated track (39) for the track subassembly (70). Calibrated millimeter scales (55, 56, 61, 62) may be embossed or printed on their upper surfaces subassembly elements. Embossed on the circular frame element (34) is a circular non-linear scale (58) that has graduations calibrated to indicate positive and negative distance differences derived from observation of cross-sectional images of the rod members (42 through 52) of reference pattern (40). The exact scales are a function of the exact geometry of the dual "X" and the pattern distance separation. Calibrated scale (59) is used in conjunction with alternate vector aid assembly (170). Planar frame element (34), and the lattice-like pattern (40) can be rotated relative to support elements (32) to bring a particular positive or negative distance difference value derived from the image cross-sectioning of reference pattern (40) into alignment with the embossed or printed arrow indicator (60) of circular support element (35). The process of determining distance difference values from a reading of imaging equipment monitor displays is more fully explained below in connection with FIGS. 10 through 13. It should also be noted that frame element (34) is provided with narrow, elongated, and essentially vertical guide surfaces (39) which are spaced apart a uniform distance and function to guide track subassemblies (70) or (170) when it is subsequently brought into cooperation with subassembly (30).

It is also important to the present invention that for each "X" pattern component in reference pattern (40) there be a prescribed included angle, as between pattern rod members (44 and 42, 46) and also as between pattern rod members (52 and 48, 50) FIG. 5. Shown in FIG. 5 as the angle a, that prescribed angle is 2 times arc tangent 0.5 or 53.130 degrees (approximately 53 degrees 8 minutes). Because of the prescribed angularity, the illustrated distances D, one of which is the distance from the principal axis (54) of reference pattern (40) to the parallel line of an equipment imaging plane designated (64) and the other of which is the distance along line (64) from the center of a rod member (44 or 50) to the center of a respective pair of rod members (42, 46 or 48, 52), are equal. Such angles in reference pattern (40) are fixed during the manufacture of planar frame element (34).

Several generally descriptive comments regarding assist apparatus (22) are appropriate at this point. All component parts are formed of materials that are compatible with the imaging system being used, either CT or MR. Most component parts may be injection molded using a transparent acrylic resin (e.g., "Plexiglas"). Those component parts having cross-sections to be imaged and displayed are filled with imaging-specific materials that are easily visualized. In the case of CT imaging, all of the components are visualized, air, metal, or plastic. For MR imaging, a suitable contrast-enhanced water or fatty material filling critical structures will suffice.

Also, and in order to develop distinctive unambiguous images for display, any of several different cross-sectional shapes or configurations may be utilized for the elements of reference pattern (40) or other critical structures (106, 108, 81, 82) that need to visualized on the image. For simplicity of illustration in this application only a rod having a rectangular cross-sectional shape is utilized. However, triangular, circular, or other cross-sectional symbols with distinctive and unambiguous shapes, or a combination of such shapes can be utilized, including wires, hollowed and filled shapes, without diminishing the utility of the invention.

Figure 6:
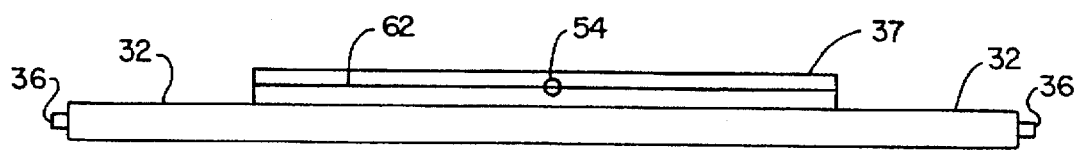
FIG. 6 is a front elevation view of the base subassembly of FIG. 4.
Figure 7:
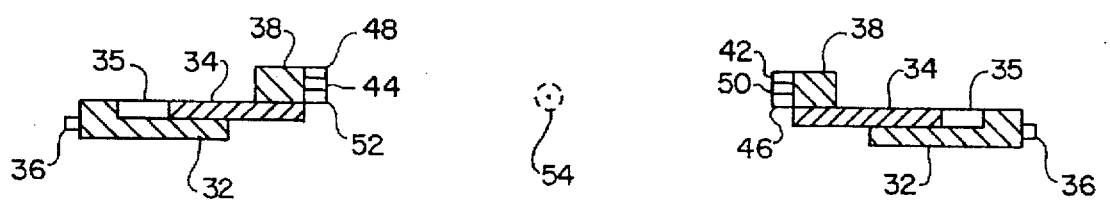
FIG. 7 is a section view taken along the line 7—7 of FIG. 4.

It should be noted in the drawings that FIG. 6 is a side elevation of base subassembly (30), and that FIG. 7 is a cross-section view through subassembly (30) taken at line 7—7 of FIG. 4. The frame element (34) and the rotatable and annular support element (35) having the reference indicia (60) are vertically recessed in the vertical extent of base element (32).

Figure 8:
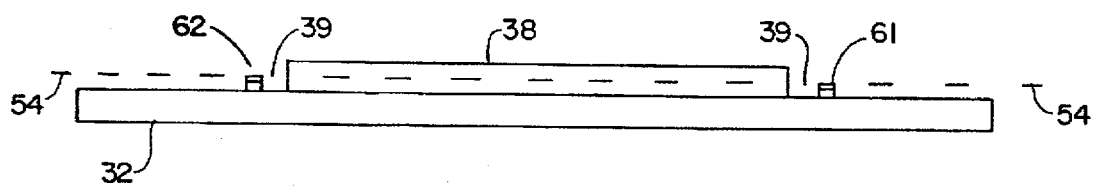
FIG. 8 is a side elevation view of the base subassembly of FIG. 4.

FIG. 8 is a side elevation of the base subassembly (30) shown in FIG. 4. The elevated frame element (38) projects above the base subassembly surface (32). The slotted interlocking surfaces are also illustrated (39).

Figure 9:
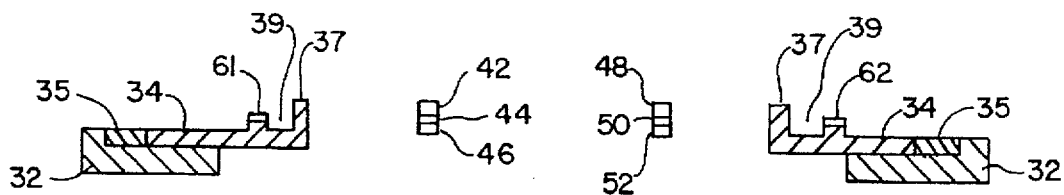
FIG. 9 is a sectioned view taken along the line 9—9 of FIG. 4.

FIG. 9 is a sectional view of the base subassembly (30) that is taken along line 9—9 of FIG. 4 and that passes through or contains the principal axis of symmetry (54) of the apparatus lattice-like pattern (40, 42, 44, 48, 50, and 52). Such lattice-like pattern, element (34), and calibrated track slots (39) rotate as a unit within the subassembly (30).

FIGS. 10 through 13 illustrate various imaging equipment screen displays that are developed as a consequence of the imaging equipment cross-sectioning image plane (14) intersecting reference pattern (40) at different angles of orientation relative to planar frame element (34). Also, for illustration purposes the magnitude of the depicted angle b is exaggerated, particularly with respect to the usual apparatus (22) initial installation using accessory support assembly (23), but may be typical of some image displays in cases where apparatus (22) is mounted directly upon the patient's body.

Figure 10:
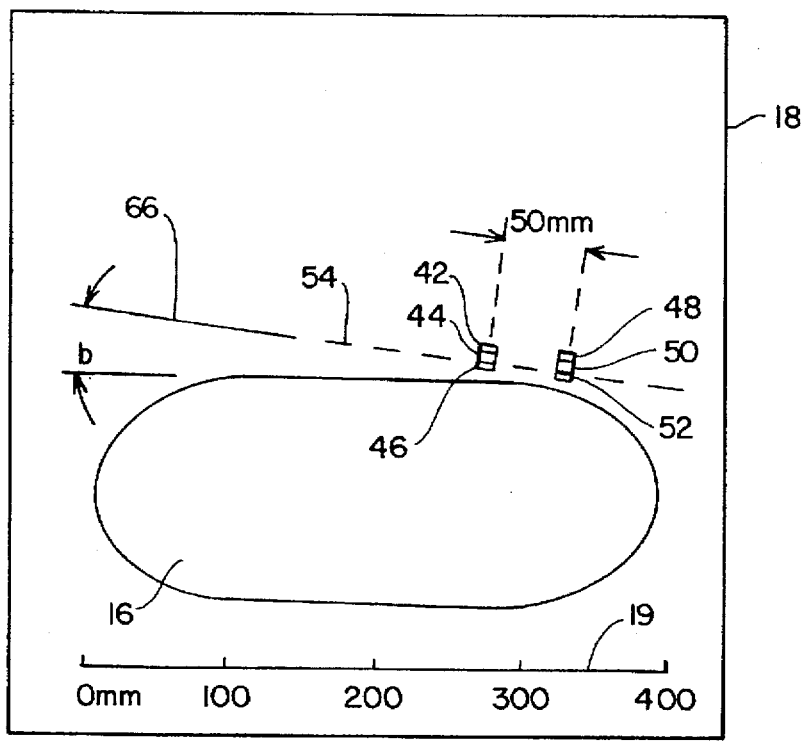
FIG. 10 is a schematic view of an imaging equipment monitor display illustrating reference images developed by an equipment imaging plane which contains the principal axis of symmetry of the base subassembly of FIG. 4.

FIG. 10 displays the image developed when the imaging equipment imaging plane (14) intersects reference pattern (40) of subassembly (34) along the pattern principal axis (54). The distance between a line intersecting the centers of rod members (42) and (46) and the center of rod member (44) along line (66) is referred to as distance A. The distance between a line intersecting the centers of rod members (48) and (52) and the center of rod member (50) along line (66) is referred to as distance B. Positive distance for A or B lie to the right of the axis of symmetry (54), while negative values are to the left on FIG. 4. The individual elements of each "X" configured pattern are separated by a zero horizontal distance along the principal axis of symmetry (54), and a sectional image of rod members (42, 44, 46) appears to the left a distance of 50 millimeters along line (66) from the sectional image of rod members (48, 50, 52). The purpose of the three different elements (44, 42, 46) is to insure accurate measurements of distance A or B independent of the orientation to the image cross section to the pattern.

The fact that line (66) is angled with respect to the equipment X-axis by the angle b is an indication that subassembly (30) has been tilted by that amount in the X-Y equipment plane from absolute level when assist apparatus (22) was positioned on patient P for subsequent use. However, that angular value does not enter into subsequent consideration during the use of apparatus (22). (Note that the determination of the 50 millimeter distance can be by measurement along line (66) on the display of monitor (18) since equipment arrangement (10) does not normally enlarge (magnify) or reduce the obtained cross-sectional image; the 50 millimeter distance therefore corresponds to the distance between the 50 millimeter graduations for sections "A" and "B" of calibrated scales (56) oriented parallel to principal axis (54)).

Figure 11:
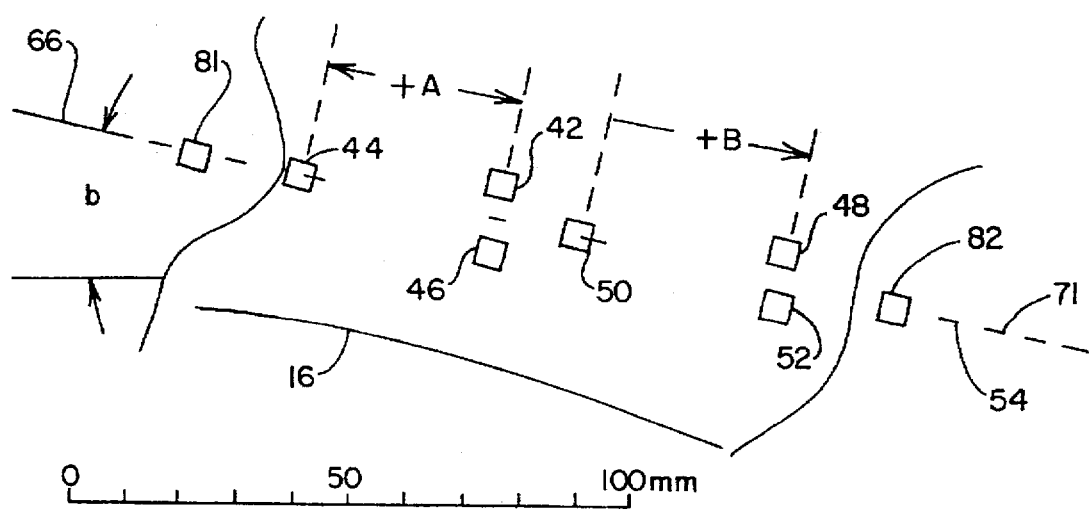
FIG. 11 is a sectioned view of the base subassembly along the line 11—11 of FIG. 4.

FIG. 11 illustrates the cross-section display developed on monitor (18) when the equipment cross-sectional imaging plane (14) intersects planar frame element (34) along section line 11—11 of FIG. 4, that line being parallel to principal axis (54). Accordingly, the angle designated c is zero (0) degrees. The cross-sectional image of rod member (44) is separated from the similar images of rod members (42 and 46) by the distance +A (distance=35 mm) along line (66) and the cross-sectional image of rod member (50) is separated from the similar images of rod members (48 and 52) by the distance B (distance=35 mm) along line (66). However, distances A and B are measured as being equal. Accordingly, the difference of (±) A minus (±) B is zero and that value on calibrated scale (58) should be set opposite indicator arrow (60). No further rotation of element (34) relative to support element (32) is required since the imaging plane intersection along sectional line 11—11 of FIG. 4 is removed from principal axis (54) by the distance A along the plane of the "double-X" reference pattern or the equal distance B. At a later stage in the use of apparatus (22), that value will be used to properly set track subassembly (70) (FIG. 14) on planar frame element (34) using the calibrated scales (61, 62) oriented transverse to principal axis (54).

Figure 12:
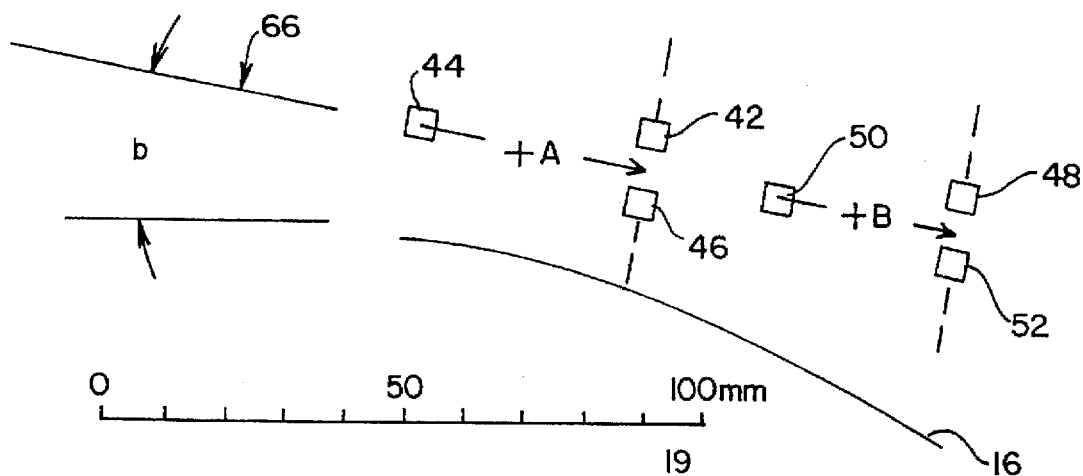
FIG. 12 is a sectioned view of the base subassembly taken along the line 12—12 of FIG. 4.

FIG. 12 depicts the display that is developed on monitor (18) when the equipment cross-sectional imaging plane (14) inter sects the plane of reference pattern (40) along the line 12—12 of FIG. 4, such line being at an angle d with respect to reference pattern (40) principal axis (54). As shown in the FIG. 10 monitor display, the distance (+) A is significantly greater than the distance (+) B, indicating that rotational adjustment of planar frame element (34) is required if principal axis (54) is to be in a plane that is parallel with the imaging equipment cross-sectional imaging plane (14). The degree of required rotation is determined by the difference of the distances (+) A and (+) B. Distance A measures +38 millimeters and distance B measures +30 millimeters, for instance, the difference of A minus B would be a positive 8 calibrated divisions. Thus, elements (34) and (40) must be rotated clockwise (FIG. 4) to a position where the +8 value of scale (58) is located at the indicator arrow (60) of support element (32) when the arrow (60) on circular track (35) was initially aligned at 0 on the scale (58). If the value of B were larger than the value of A, then the difference would be a negative value and the reference pattern plane would require rotation in a counter-clockwise direction to a negative scale value.

Figure 13:
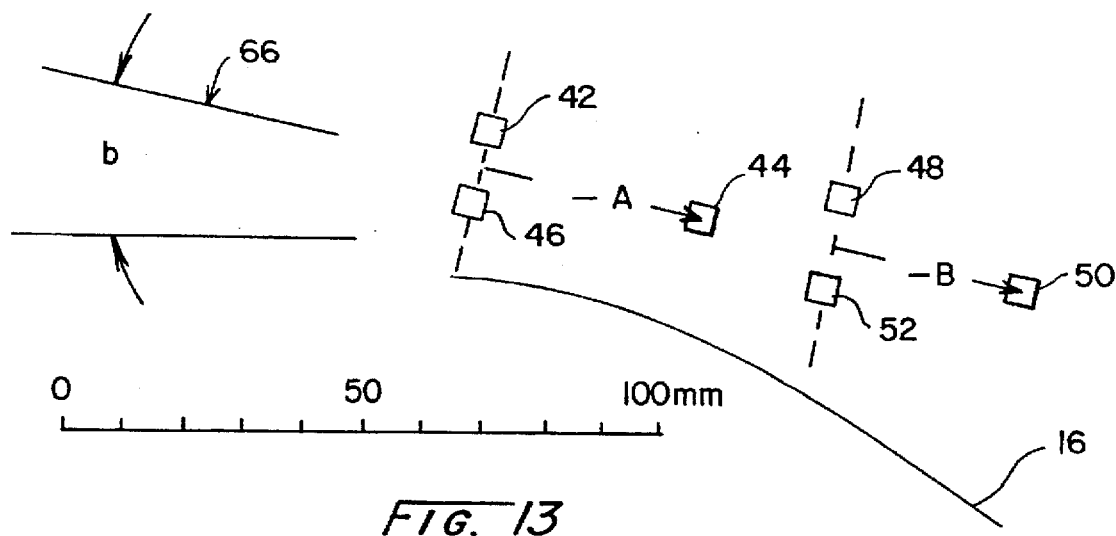
FIG. 13 is sectioned view of the base subassembly taken along the line 13—13 of FIG. 4.

Another example of an equipment monitor display developed by a practice of this invention is provided in FIG. 13. This particular display differs from the other examples in that the imaging equipment cross-sectional imaging plane (14) intersects the positioned assist apparatus along the line 13—13 of FIG. 4 with the degree of angularity being indicated by the angle e. In this particular case, the distance A measures (−) 37 millimeters and the distance B measures (−) 34 millimeters for an A minus B (difference) value of −3 calibrated steps. Such indicates that planar frame element (34) should be rotated counter-clockwise so that the −3 graduation of calibrated scale (58) is aligned with indicator arrow (60) that was preset to 0 on the calibrated scale (58). Such would then result in principal axis (54) of subassembly element (34) potentially being in a plane that is parallel to the imaging equipment X-Y or cross-sectional imaging plane (14).

From the foregoing it can be appreciated that the primary function of apparatus subassembly (30), after being initially positioned on or adjacent to the patient P, is to provide a means for subsequently establishing the angle of intersection with, and the distance from the principal axis of the device to the equipment cross-sectional image plane. The subassemblies can be subsequently rotated and translated exactly to then coincide with the equipment imaging plane (FIG. 11). It should also be noted with respect to FIGS. 10 through 13 that if base subassembly (30) is initially positioned on patient P to be parallel with the X-Z coordinate plane of imaging equipment (10), the angle designated b is zero and the images of rod members (42 through 52) would be displayed along a horizontal (X-direction) line rather than as presently positioned in such Figures.

Figure 15:
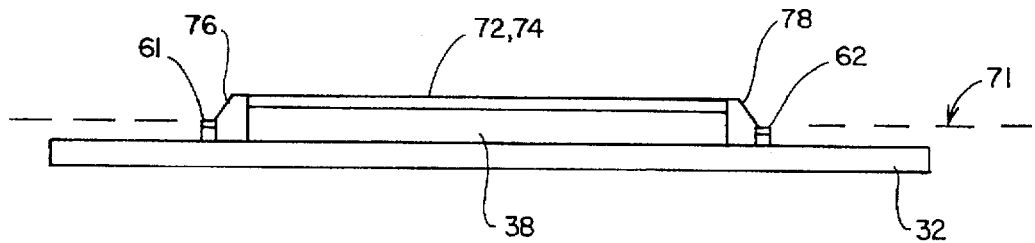
FIG. 15 is a elevation view of the base subassembly of FIG. 4 and the track subassembly FIG. 14 assembled.

Following adjustment rotation of subassembly element (34) relative to subassembly element (32) (if necessary), the track subassembly (70) of FIGS. 15, 14 is properly positioned on the base subassembly (30) previously placed on patient P FIG. (15). As described below, this act in essence physically locates, slightly above the patient's body, the position of the intersection path of the imaging equipment vertical cross-sectional imaging plane (14) on subassembly (30) when that imaging plane "slices" the patient's anatomical target of interest.

Track subassembly (70) is comprised of parallel and spaced apart upper guide elements (72 and 74) which are mounted upon and fixedly secured to parallel and spaced-apart lower guide elements (76 and 78). Elements (76 and 78) are spaced apart a distance adequate to glide within the groove guide (39) between elements surfaces (37, 61, 62) built into the frame portion of rotatable planar frame element (34). Also provided in track subassembly (70) are the indicator arrows (80) indicating its axis of symmetry (71). An embossed sliding linearly calibrated millimeter scale (84) is incorporated into element (72). Arrows (80) are preferably embossed on the upper surfaces of guide elements (76 and 78) and are each centered between guide elements (72 and 74). Small linear cavities (81, 82) with conspicuously image apparent materials are incorporated into the gliding track elements (76, 78). These are used to confirm on the image (18) that the axis of symmetry (71) of the track subassembly (70) is within the image section (14) FIG. (11). Subassemblies (30 and 70) cooperate with each other. To properly place subassembly (70) on subassembly (30), indicator arrows (80) are aligned with the positive or negative values on transverse scale (61, 62) set with their 0 distance aligned with the axis of symmetry (54). The distance on the calibrated scales (61, 62) corresponds to either the distance (A) or the equal distance (B) as measured on monitor display (18) when the principal axis of symmetry (54) and image plane (14) are parallel. When the track subassembly is moved to the measured distance A or B then the axis of symmetry (71) of the track subassembly will be within the image plane section (14).

FIG. 15 is a side elevation view of the track subassembly (70) and the base subassembly (30) in their assembled relation.

Figure 16:
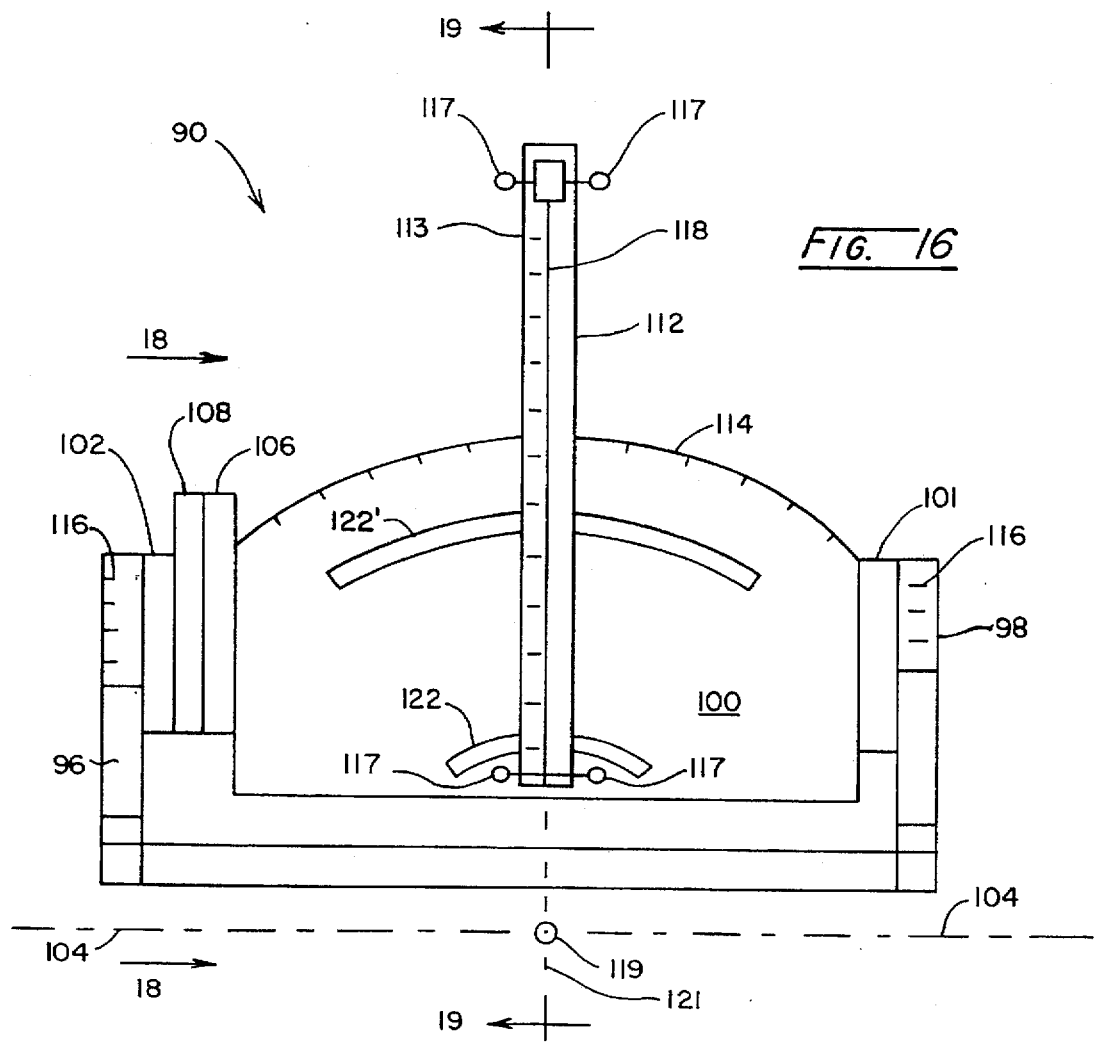
FIG. 16 is a side elevation view of the vectoring aid subassembly incorporated into the assist apparatus of FIG. 3.
Figure 18:
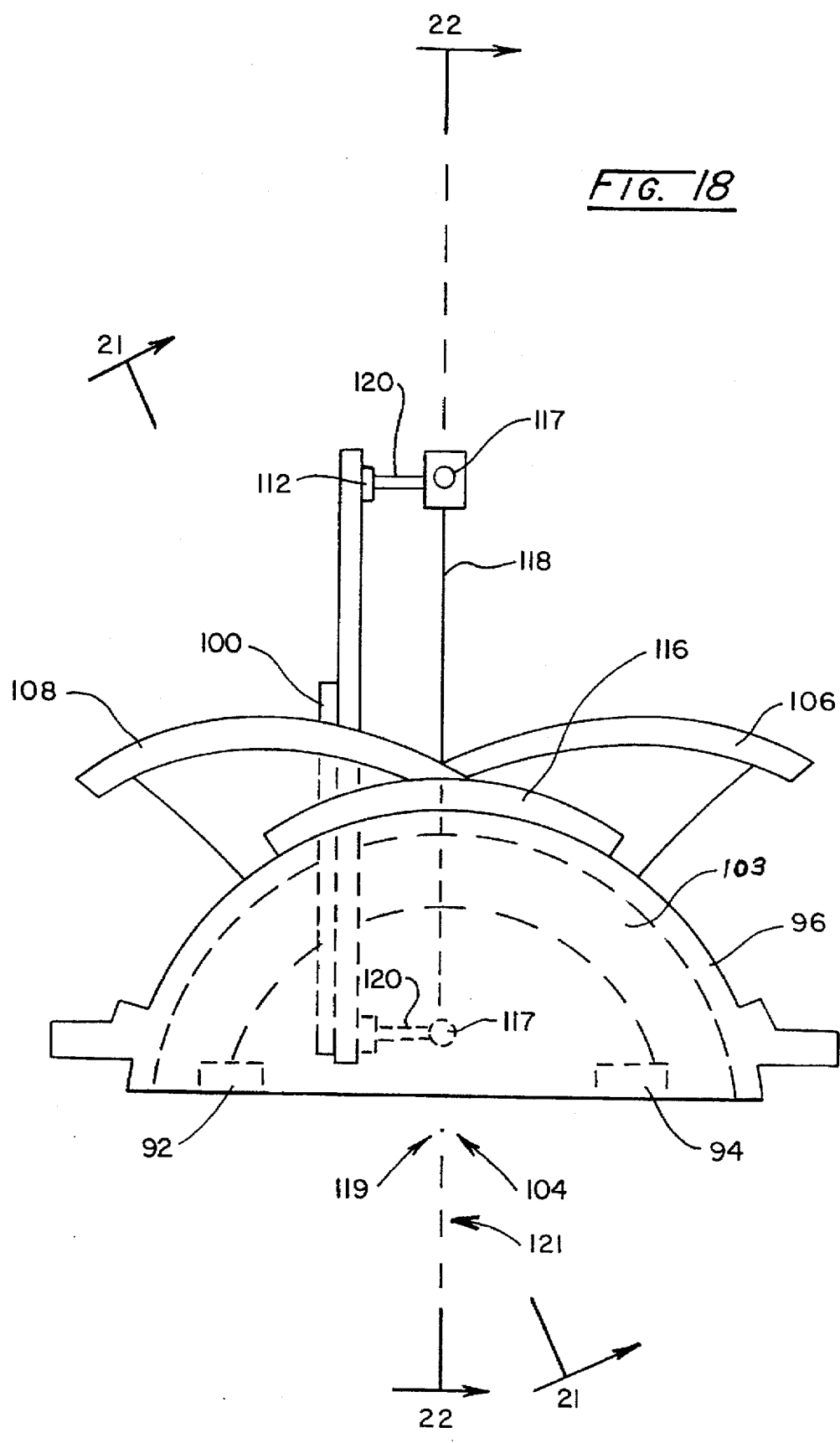
FIG. 18 is an end elevation view of the vectoring aid subassembly taken along line 18—18 of FIG. 16, FIG. 17.
Figure 23:
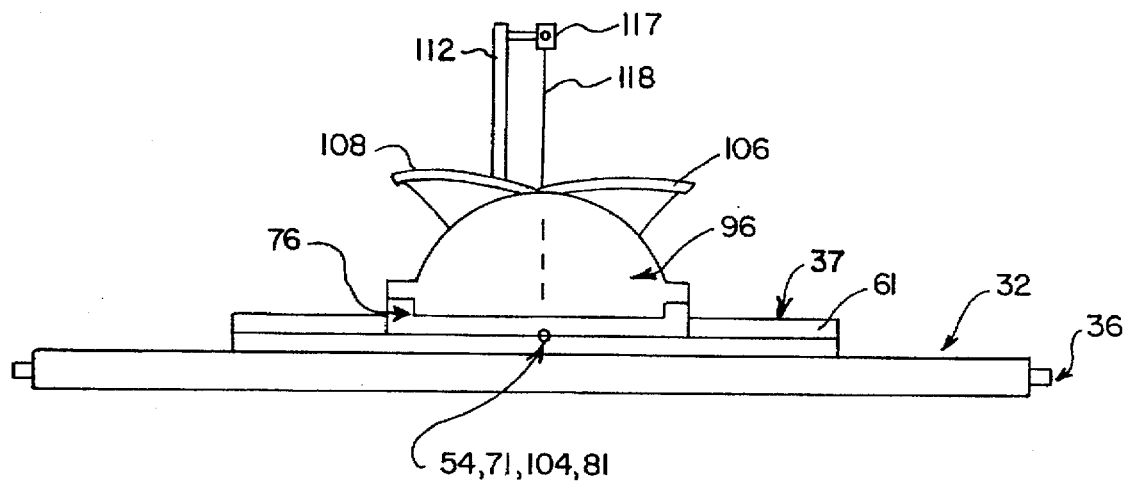
FIG. 23 is an end elevation view of the complete assembled invention including the base subassembly, track subassembly, and the vectoring aid subassembly.
Figure 24:
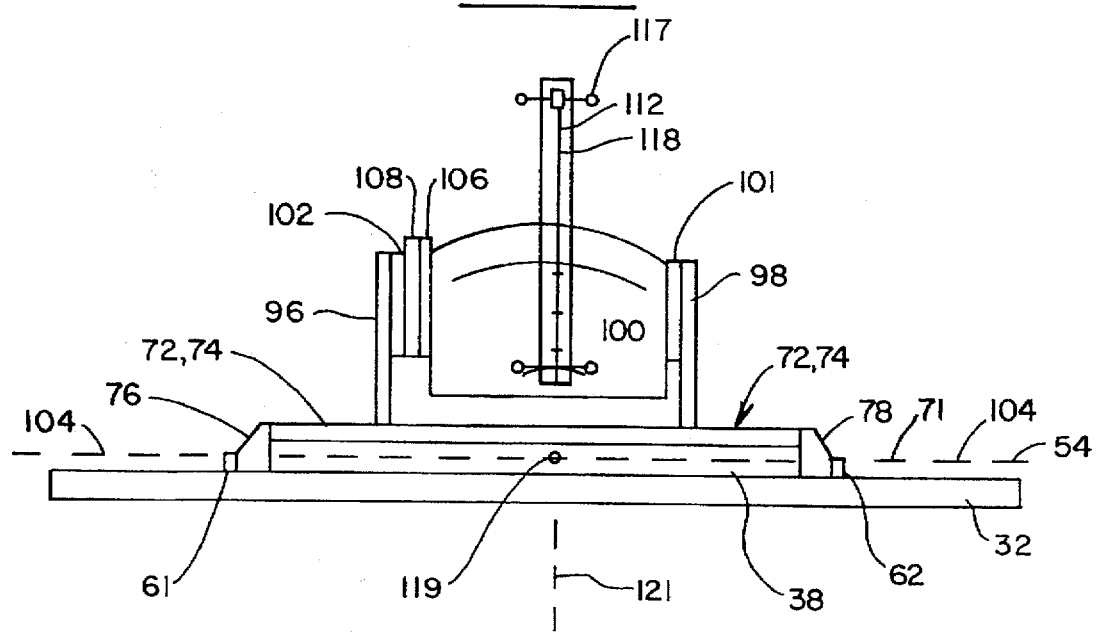
FIG. 24 is a front elevation view of the complete invention including the base subassembly, track subassembly, and the vectoring aid subassembly.

FIGS. 16 through 22 detail the vectoring aid subassembly (90) that is next appropriately placed on track subassembly (70) and adjusted, if necessary, to accommodate a second direction of tilt of subassembly (30) relative to the imaging equipment X-Z coordinate plane (14). It also supports and conspicuously displays on the image the location of the needle like device and its' vector path. FIG. 16 is a front elevation view of vector aid subassembly (90).

Subassembly (90) is essentially comprised of a rigid frame made up of lateral guide elements (92 and 94) joined to vertical end-piece elements (96 and 98), and a movable composite adjustable vectoring plane support member (100). Vectoring plane member (100) is fixed to multiple components and moves as a unit, including the arc track supports (101, 102), and the warped "X" pattern plane (106, 108). These elements are frictionally mounted in the rigid frame end-piece elements (96 and 98) at each extreme by elements (101, 102). These have circular arc tracks that glide over interlocking arc projections (103, 105) of side support element (96, 98). These move as a unit centered on the axis of rotation (104).

A movable needle or physical vector pointer (118) is mounted on a needle, vector track guide (112) parallel to the vector plane surface (100). On the vector track guide is a calibrated mm scale (113). The needle is held within the plane of the vector track guide (112) at all times by sliding guides (120). The movable needle track guide (112) glides in arc detents (122', 122) on the surface of the vector plane surface (100). The guides (120) and the needle track guide (112) direct the needle to a single point at the center of needle rotation (119). This lies outside the vector subassembly (90) and is centered at the level of the axis of symmetry (54) for the base subassembly (30) and the axis of rotation (104) of the track subassembly (70). The angle of the needle track guide (112) is embossed on the surface of the vector plane surface (100) on a protractor-like pattern (114). Movable needle guide (120) slide along the needle track guide (112). Guide (112) fixes the direction and stability of the needle and vector path. Integral to the movable needle vector supports are the image visible needle markers (117). These are small chambers filled with material conspicuously visible on the image display (18). The needle markers can move with the needle confirming on the image the exact location of the needle or vector.

On the upper margin of the track supports (101) and (102) are embossed arrows (109, 110) aligned with the plane of the path of the vector pointer (118). Along the upper arc surfaces of the lateral side supports (98, 96) are movable arch-shaped embossed scales (116) in calibrated linear distances equivalent to calibrated degrees. The movable scales (116) are aligned to a 0 value with the arrows (109, 110) on the arc supports (101, 102) prior to rotation of the vector plane (121). Scale (116) may be calibrated in units such as millimeters that correspond to the angularity displacement units encoded by the distance between warped X visible components (106, 108) on the image (18) in the cross-sectional image (14). Examples of the range of pattern cross-sectional images that may be displayed are provided in FIG. 20 through the axis of rotation (104).

Vectoring plane member (100) is joined with image visible reference pattern members (106, 108) and track supports (101, 102) and needle (118) to move as a unit around the axis of rotation (104). The comprised curve elements (106 and 108) together constitute a planar reference pattern with a hereinafter-described bi-plane "warped-X" image conspicuously apparent pattern plane configuration. The outer margin of the curved reference pattern members (106, 108) are chambers filled with image conspicuous material similar to the rods (42, 52, 80). It is the cross-sectional image of reference pattern members (106, 108) appearing on the imaging equipment monitor display (18) that indicates the magnitude and direction of required rotational correction for member (101, 102) or indicated that no rotational correction is required if such is the case.

The "warped-X" reference pattern developed by the complex curved upper surfaces of reference pattern elements (106 and 108) is based on a similar principle that is utilized in the development of each of the X-patterns in the "double-X" reference pattern configuration (40) of FIG. 4 except that it corresponds to a radially calibrated motion path. See particularly FIG. 5. For example, using a pattern base radius of 5.73 centimeters (57.3 millimeters or 2.25 inches), which would correspond to the radius of the upper cylindrical surface of end-piece element (96) in FIG. 21, each millimeter of circumferential displacement of vectoring plane element (100) to either side of the relatively vertical initial plane position of FIG. 18 will produce an additional millimeter distance between the centers of the curved reference pattern elements (106 and 108). It is this encoded radial disparity that is displayed in the additional cross-sectional image that is included in the display of equipment monitor (18) following the placement of subassembly (90) on subassembly (30) and proper repositioning of patient P and super imposed assist apparatus (22) in imaging equipment (10) plane (14).

It should be noted in connection with subassembly (90) that the units of displacement embossed or printed on circumferential scale (116) should correspond to the distance separation developed in the cross-section images of transverse reference pattern member (106, 108). However, other scaling relationships than that utilized in connection with the immediately above example might be necessarily or advantageously utilized depending upon particular imaging equipment monitor display characteristics.

FIGS. 21 and 22 illustrate equipment monitor (18) displays relating to the use of vectoring aid subassembly (90). Referring to FIG. 21, the image of reference pattern elements (106 108) indicates that needle element (118) intersects, and accordingly is not fully or completely within, equipment cross-sectional image plane (14). Rotation of elements (101, 102, 106, 108, 118) as a unit is required and the amount and direction of rotation are determined from a measurement of the distance disparity between the images of elements (106 and 108) on the monitor display and as to whether reference pattern plane element (106) is higher or lower than reference pattern plane element (108). The 0 degree on the movable degree scales (116) are first centered on the arrows (109, 110). See FIG. 17. Upon effecting rotation of vectoring aid plane elements (101, 102, 118) sufficiently to compensate for the detected base assembly (30) tilt about the axis of rotation (104), the new composite sectional image of the "warped-X" reference pattern combined elements (106, 108, 118) will appear in the form indicated in the monitor (18) display of FIG. 22 with the needle parallel and within the image location (14).

Also with respect to FIG. 22, the angle designated f, the angular magnitude of which may be determined in any instance through use of a protractor-like overlay for the display of monitor (18), indicates the desired angle of the path from opening to target T relative to a line perpendicular to line (66) associated with reference pattern (40). The vector aid subassembly can be moved along the track to the exact chosen location using the sliding mm distance scale (84) of the track subassembly (70).

Lastly, and assuming the using physician has positioned vectoring aid subassembly (90) parallel to the image (14) and is properly located along track subassembly (70), the instrument is aligned with the angular value f of scale (114) embossed or printed on vectoring aid plane element (100), and the needle (118) or instrument then advanced downward along the linear needle path (112) for penetration into the body of patient P to reach chosen target point T along the chosen vector path (121) in a minimum number of steps. Verification of accurate medical instrument penetration progress may be made from time to time by the operating physician by effecting an image update on equipment monitor (18). Depth of penetration can be controlled by the calibrated needle track scale (113).

Figure 25:
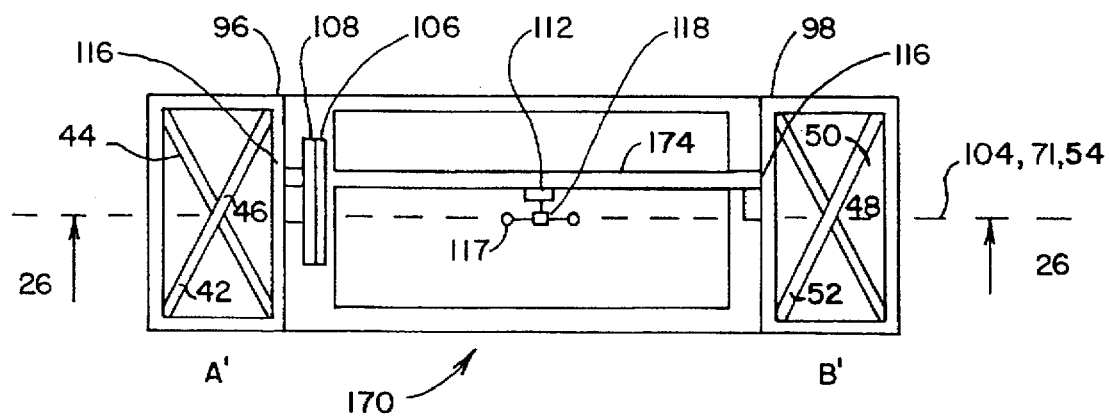
FIG. 25 is a plan view of an alternate track and vectoring aid subassembly combining invention reference patterns, a track, and instrument vectoring guide elements in a different manner for use with the base subassembly of FIGS. 4.
Figure 26:
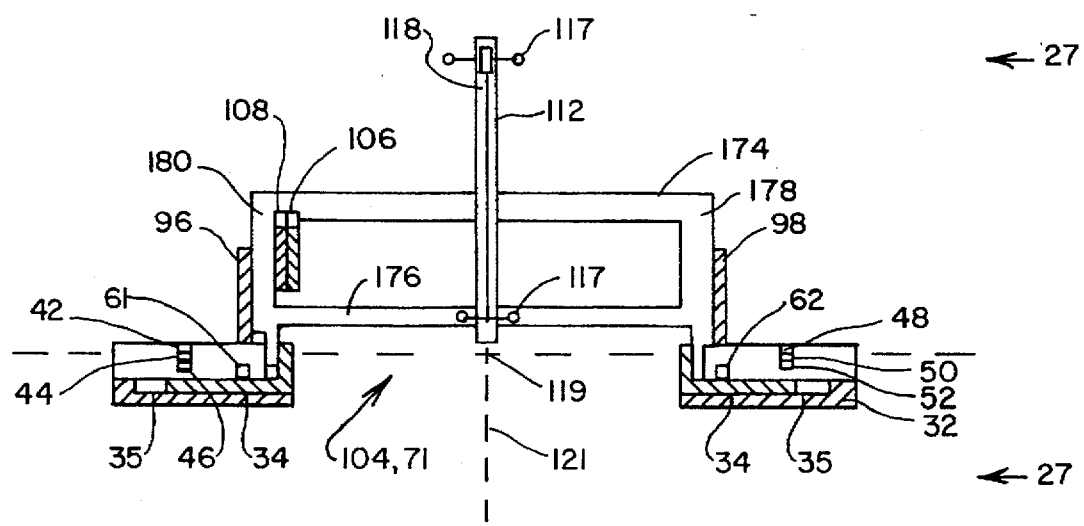
FIG. 26 is a partially sectioned front elevational view of the assembled alternate invention taken at line 26—26 of FIG. 25.
Figure 27:
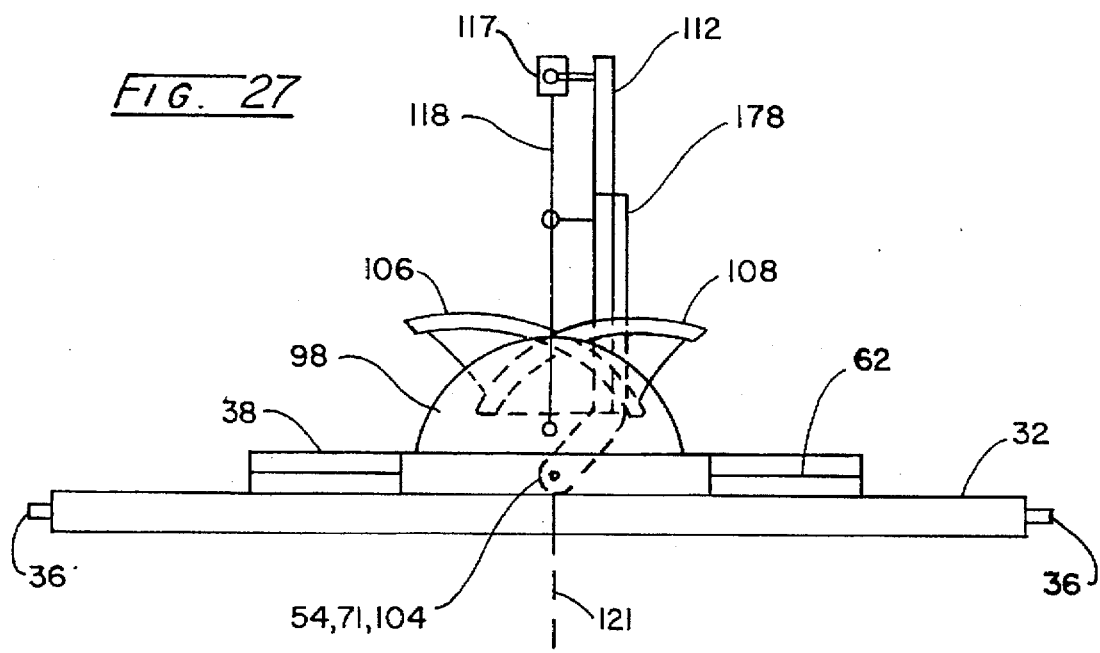
FIG. 27 is an end elevation view of the assembled alternate invention of FIGS. 25 and 26.

FIGS. 25 through 27 illustrate the subassemblies of a second embodiment of the assist apparatus of the present invention. Such alternate embodiment, is comprised of a combined track and vector aid subassembly (170) used with the base subassembly (30). Since the alternate embodiment utilizes component elements which perform the same function as the corresponding elements of apparatus (22), the same component reference numerals used in FIGS. 1 through 24 are also used in FIGS. 25 through 27.

The base subassembly (170) could differ primarily in that it does not include a central planar reference pattern, such as pattern (40). In the alternate embodiment the functional equivalent of that reference pattern is combined into subassembly (170). Thus, the interior area of frame portion (37, 38) could become completely open and there is no included structure to perchance interfere with the manual insertion of a medical instrument used for patient treatment. Also, calibrated movable reference millimeter scales (61, 62) are positioned to facilitate use in cooperation with subassembly (170). As commented below, the positioning of the elements of planar reference pattern (40) in the subassembly (170) configuration tends to obscure a scales (55, 56) positioned as shown in the FIG. 4 embodiment. These "X" patterns are moved to the periphery, but function in a similar fashion. They are moved to align the axis of symmetry (54) of vectoring guide subassembly (170) to the image section plane (14).

The vectoring guide subassembly (170) of FIGS. 25 and 26, along with the functioning of planar reference plane (40), accomplishes the functions of previously discussed subassemblies (70 and 90) but with a different arrangement, and sometimes different form, of component parts.

For instance, whereas previously the vectoring aid subassembly (90) was moved as a unit along the longitudinal axis of track subassembly (70), in the embodiment designated (170) only an instrument needle track element (112) is adjustable and translatably moved relative to the longitudinal axis of subassembly (170) by lateral movement along and rotational movement relative to support bar elements (174 and 176). Support bar elements (174 and 176) are integrally joined at their respective ends by up right support bars (178 and 180). These elements rotate through their axis of rotation (104) through axial pin connections. Arrows are embossed on the sides of vertical supports (178, 180) and the movable scales (116) are embossed on lateral arc supports (96, 98). Thus elements (174, 176, 178, 180, 118, 112) function as an adjustable vectoring plane member. The movable linear millimeter scales (61, 62) of the base subassembly (30) are used to position the location of the axis of rotation (104) and axis of symmetry (54) of the vectoring subassembly (170) within and parallel to the image plane (14). The scale (59) for calibrated degrees of rotation of the alternate vectoring aid device (170) would be calibrated to the distance difference separating the dual "X" pattern A' and B' lattice rods (40, 42, 46, 48, 50, 52).

Figure 28:
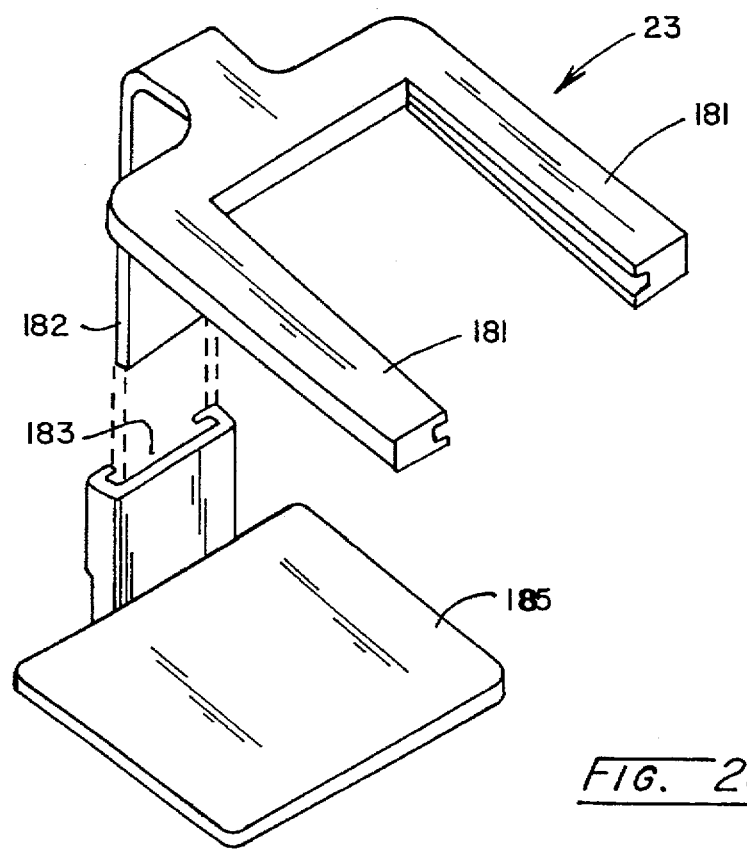
FIG. 28 is a perspective illustration of one form of an adjustable accessory support assembly that may be utilized to locate either of the illustrated embodiments of my invention in proximity to the region of interest of a patient's body.

FIG. 28 is an oblique elevation for accessory support assembly (23) of FIG. 3. Assembly (23) is essentially comprised of a base (185) and joined support arms (181). Each support arm (181) has a longitudinal groove which receives and cooperates with a tongue (36) of base subassembly (30). Elevation adjustment of support arms (181) is achieved by the adjustment of cooperating "tongue and groove" elements (182 and 183). Base (180) may be fixedly secured in its position by attachment to equipment table (12) or may be temporarily secured in its position by placement between table (12) and the patient's body.

Other materials, component shapes, and component sizes may be utilized in the practice of this invention as claimed.

I claim my invention as follows:

1. Apparatus for utilization in a medical procedure that also involves the use of medical imaging equipment having a cross-sectional imaging plane and a monitor which displays a patient cross-sectional image currently being taken at the equipment cross-sectional imaging plane, and comprising:

an apparatus base member adapted to be placed in a position that is stationary relative to a patient's body target of interest and that intersects the medical imaging equipment cross-sectional imaging plane;

an apparatus frame member being supported by and rotatable about a substantially vertical axis relative to said apparatus base member;

a reference pattern carried by said apparatus frame member, having a principal axis and having pattern elements comprised of a material and size for placement and imaging at the medical imaging equipment cross-sectional imaging plane and visibly displayed in cross-section on the medical imaging equipment monitor to provide linear measurements proportionally indicating on the medical imaging equipment monitor an angular position and separation distance of said reference pattern principal axis relative to the medical imaging equipment cross-sectional imaging plane;

a graduated angular position scale affixed to one of said apparatus base member and said apparatus frame member; and a position indicator element co-operating with said graduated angular position scale and affixed to the other of said apparatus base member and said apparatus frame member to indicate an angular position of said frame member.

2. The apparatus defined by claim 1 wherein said reference pattern has an interior area through which at least portions of a medical instrument may be passed, said reference pattern interior area being defined in part by portions of said reference pattern elements.

3. The apparatus defined by claim 2 wherein said reference pattern elements are integral with said apparatus frame member.

4. The apparatus defined by claim 1 further comprising a graduated linear distance position scale.

5. The apparatus defined by claim 1 wherein said reference pattern elements are configured in a double-X pattern that is centered with respect to said reference pattern principal axis, said double-X configured pattern elements when imaged comprising one spaced-apart pair of unified elements displayed on the medical imaging equipment monitor when said reference pattern principal axis is contained within the medical equipment cross-sectional imaging plane.

6. The apparatus defined by claim 1 wherein said reference pattern elements are configured in a double-X pattern that is centered with respect to the reference pattern principal axis, when imaged said double-X configured pattern elements forming two spaced-apart pairs of spaced-apart elements displayed on the medical imaging equipment monitor when said reference pattern principal axis is positioned away from the medical imaging equipment cross-sectional imaging plane.

7. The apparatus defined by claim 6 wherein said reference pattern elements include pattern elements which intersect each other at an angle of approximately fifty-three degrees.

8. The apparatus defined by claim 6 wherein said two spaced-apart pairs of spaced-apart element sectional images are each comprised of equally spaced-apart elements, when imaged said equally spaced-apart elements appearing on the medical imaging equipment monitor when said reference pattern principal axis is contained in a plane that is parallel to the medical imaging equipment cross-sectional imaging plane.

9. The apparatus defined by claim 8 wherein the displayed linear measurements of one of said spaced-apart pairs of spaced-apart elements describe the distance between said reference pattern principal axis and said medical imaging equipment cross-sectional imaging plane.

10. The apparatus defined by claim 8 and further comprising a medical instrument guide support track carried by and movable with respect to said apparatus frame element and having a longitudinal guide and two points which prescribe the orientation of a reference longitudinal straight line, said guide support track being positioned on said apparatus frame element in a manner whereby said reference longitudinal straight line is separated from said medical imaging equipment cross-sectional imaging plane by either of the equal distances indicated by said equally spaced-apart pattern element sectional image displayed on the medical imaging equipment monitor.

11. The apparatus defined by claim 6 wherein said two spaced-apart pairs of spaced-apart elements are each comprised of differently spaced-apart elements when imaged said pairs of differently spaced-apart elements appearing on the medical imaging equipment monitor when said reference pattern principal axis is positioned angularly with respect to the medical imaging equipment cross-sectional imaging plane.

12. The apparatus defined by claim 11 wherein the numerical difference between the displayed linear measurements of said spaced-apart pairs of spaced-apart elements describe the angularity on said graduated angular position scale between said reference pattern principal axis and said medical imaging equipment cross-sectional imaging plane.

* * * * *